United States Patent
Garms et al.

(10) Patent No.: US 7,492,856 B2
(45) Date of Patent: Feb. 17, 2009

(54) APPARATUS AND METHOD FOR PROVIDING AN ORTHOGRAPHIC PROJECTION FROM HELICAL SCAN DATA

(75) Inventors: Walter I. Garms, Berkeley, CA (US); Ugo Di Girolamo, Fremont, CA (US); Matthew Merzbacher, Oakland, CA (US)

(73) Assignee: GE Security, Inc., Bradenton, FL (US)

( * ) Notice: Subject to any disclaimer, the term of this patent is extended or adjusted under 35 U.S.C. 154(b) by 0 days.

(21) Appl. No.: 11/295,954

(22) Filed: Dec. 7, 2005

(65) Prior Publication Data

US 2007/0140415 A1 Jun. 21, 2007

(51) Int. Cl.
A61B 6/03 (2006.01)

(52) U.S. Cl. .............................. 378/15; 378/4; 378/901; 378/19

(58) Field of Classification Search ...................... 378/4, 378/15, 19, 901, 13, 14, 57
See application file for complete search history.

(56) References Cited

U.S. PATENT DOCUMENTS 5,182,764 A   1/1993   Peschmann et al. ............ 378/57

(Continued)

FOREIGN PATENT DOCUMENTS

DE   198 32 276 A1   1/2000

EP   0 428 348 A2   11/1990

(Continued)

OTHER PUBLICATIONS

"Total Effective Radiation Dose from Spiral CT and Conventional Radiography of the Pelvis with Regard to Fracture Classification" by A.G. Lurik, L. C. Jensen and J. Hansen, Acro Radiologica 37 (1996) pp. 651-654 and 2 pgs of Figures.

(Continued)

Primary Examiner—Hoon Song
(74) Attorney, Agent, or Firm—Eugene Hyun, Esq.; Armstrong Teasdale LLP

(57) ABSTRACT

An apparatus and method for providing a projection image directly from data acquired by a CT scanner, the method comprising: acquiring an amount of data corresponding to an entire object that is scanned by the CT scanner, wherein the amount of data is generated by an x-ray source that projects a fan beam of x-rays toward a detector array on an opposite side of a gantry of the CT scanner as the object is passed through an opening in the gantry; selecting an imaging plane, the imaging plane corresponding to a view of the object; dividing the imaging plane into a plurality of rows and columns, thus creating a grid of points corresponding to the imaging plane; determining, for each point in the grid, a data point from the acquired data corresponding to an x-ray source position wherein a ray from the x-ray source to the grid point is closest to a perpendicular orientation with respect to the imaging plane, and a detector position where the ray intersects the detector array; and presenting a projection image corresponding to the selected imaging plane, wherein the projection image comprises a plurality of projection points and each projection point in the projection image is a converted value of the data points of the data points of the acquired data.

31 Claims, 10 Drawing Sheets

U.S. PATENT DOCUMENTS

| | | | |
|---|---|---|---|
| 5,233,518 A | 8/1993 | King et al. | 364/413.18 |
| 5,367,552 A | 11/1994 | Peschmann | 378/57 |
| 5,668,846 A | 9/1997 | Fox et al. | 378/4 |
| 5,708,690 A | 1/1998 | Hsieh | 378/4 |
| 5,796,803 A | 8/1998 | Flohr et al. | 378/15 |
| 5,946,371 A | 8/1999 | Lai | 378/19 |
| 5,960,056 A | 9/1999 | Lai | 378/4 |
| 6,038,278 A | 3/2000 | Hsieh et al. | 378/15 |
| 6,108,575 A | 8/2000 | Besson | 600/425 |
| 6,229,869 B1 * | 5/2001 | Hu | 378/4 |
| 6,459,756 B1 | 10/2002 | Tam et al. | 378/15 |
| 6,647,084 B1 | 11/2003 | Hsieh | 378/4 |
| 2004/0131140 A1 * | 7/2004 | Bruder et al. | 378/4 |

FOREIGN PATENT DOCUMENTS

| | | |
|---|---|---|
| EP | 0 969 414 A2 | 1/2000 |
| EP | 1 396 820 A1 | 3/2004 |
| JP | 5-23329 | 2/1993 |
| JP | 6-38959 | 2/1994 |
| JP | 2003-164444 | 6/2003 |
| WO | WO 99/01067 | 1/1999 |

OTHER PUBLICATIONS

"Storing Medical Images on High Density Digital Tape Recorders" by Gerald J. Wade, SPIE vol. 416, Picture Archiving & Communication Systems (PACS II) for Medical Application (1983), pp. 36-41.
Minimum Detection Windows, PI-line Existence and Uniqueness for Helical Cone-Beam Scanning of Variable Pitch, 2004 American Associate of Physicists in Medicine, Med. Phys. 31 (3), Mar. 2004, pp. 566-572.

* cited by examiner

90 Degrees  30 Degrees  60 Degrees

APPARATUS AND METHOD FOR PROVIDING AN ORTHOGRAPHIC PROJECTION FROM HELICAL SCAN DATA

BACKGROUND

This present invention relates generally to an apparatus and method for scanning and inspecting baggage. More particularly, the present invention relates to an explosive detection system (EDS).

Carry-on and checked baggage inspection systems generally utilize a scan projection (SP) image for presentation to the operator. In most baggage inspection systems, scan projection images are created by moving an object under a fan beam of x-rays from a stationary x-ray source. X-ray intensities, after being attenuated by the object being scanned, are measured by an array of detectors. The x-ray intensity data is converted through a process called normalization so that each pixel represents approximately the total mass traversed by the ray. SP images may be difficult to interpret because they are an orthographic projection in one direction (the direction of bag travel), but are a perspective projection in the other direction (across the x-ray fan).

In some computed tomography (CT) imaging system configurations, an x-ray source projects a fan-shaped beam which is collimated to lie within an X-Y plane of a Cartesian coordinate system and generally referred to as an "imaging plane". The x-ray beam passes through an object being imaged. The beam, after being attenuated by the object, impinges upon an array of radiation detectors. The intensity of the attenuated radiation beam received at the detector array is dependent upon the attenuation of the x-ray beam by the object. Each detector element of the array produces a separate electrical signal that is a measurement of the beam intensity at each detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray fan beam intersects the object constantly changes. A group of x-ray attenuation measurements (e.g., projection data), from the detector array at one gantry angle is referred to as a "view". A "scan" of the object comprises a set of views made at different gantry angles, or view angles, during one revolution of the x-ray source and detector about the object or patient being imaged.

Many modern CT systems are helical scanners (also known as spiral scanners), in which the scanned object is continually moved while the projection data is being acquired. The path of the X-Ray source describes a helix with respect to the scanned object. Most helical scanners have multiple rows of detectors, and the x-ray fan is collimated into a cone to illuminate the entire array of detectors. The angle between the x-ray source and the first and last detector rows is referred to as the "cone angle".

The entire scanned volume scanned by the helical scanner can be reconstructed using well known tomographic reconstruction algorithms such as direct Fourier or filtered back projection methods, and more exact methods described by FeldKamp and Katsevich. All of these techniques require a very large amount of computation.

Orthographic and SP-like images can be created from the reconstructed volumetric data by projecting digitally through the reconstructed data. This requires significant additional computation, and the resulting projection may not have as much resolution as the original scan data.

Projection images (also known as radiographic images) are required for EDS operator resolution, and also may be used to select a limited number of planes that need to be reconstructed from the helical data. A helical scanner produces data that can be used to reconstruct a volume, but does not directly produce a readable projection image. Reconstruction of the volume, and then creating a projection through the volume as discussed above requires a very large amount of computation, and the result may have limited resolution.

Accordingly, it is desirable to provide an apparatus and method for creating a projection image directly from the helical scan data.

SUMMARY OF THE INVENTION

An apparatus and method for providing a projection image directly from data acquired by a CT scanner, in one embodiment a computed tomography system for providing a scan projection image directly from data acquired by the system is provided. The system comprising: a CT scanner, configured to produce x-ray projection data as an object is passed through the CT scanner; a storage medium encoded with machine readable computer program code for providing a scan projection image of an imaging plane of the x-ray projection data, the storage medium including instructions for causing a computer to implement a method comprising: acquiring an amount of data corresponding to an object that is scanned by the CT scanner, wherein the amount of data is generated by an x-ray source that projects a fan beam of x-rays toward a multiple row detector array on an opposite side of a gantry of the CT scanner as the object is passed through an opening in the gantry, the acquired amount of data comprising a reconstruction volume; selecting a portion of a plane intersecting the reconstruction volume, wherein the selected portion comprises an imaging plane, the imaging plane corresponding to a view of the object; dividing the imaging plane into a plurality of rows and columns creating a plurality of points corresponding to the imaging plane; for each point on the imaging plane determining an x-ray source position and a detector position wherein the ray from the x-ray source to the detector is the closest to a perpendicular orientation with respect to the imaging plane and wherein the x-ray source position may be on either side of the imaging plane; selecting the corresponding data point from the converted helical scan data; and presenting a projection image corresponding to the image plane, wherein the projection image represents a near orthographic projection through the object onto the imaging plane.

A storage medium encoded with machine readable computer program code for providing a scan projection image of an imaging plane of the x-ray projection data, the storage medium including instructions for causing a computer to implement a method comprising: acquiring an amount of data corresponding to an object that is scanned by the CT scanner, wherein the amount of data is generated by an x-ray source that projects a fan beam of x-rays toward a multiple row detector array on an opposite side of a gantry of the CT scanner as the object is passed through an opening in the gantry, the acquired amount of data comprising a reconstruction volume; selecting a portion of a plane intersecting the reconstruction volume, wherein the selected portion comprises an imaging plane corresponding to a view of the object; dividing the imaging plane into a plurality of rows and columns, thus creating a grid of points corresponding to the imaging plane; determining, for each point in the grid, a data point corresponding to an x-ray source position wherein a ray from the x-ray source is closest to a perpendicular orientation with respect to the imaging plane, and a detector position where the ray intersects the detector array; and presenting a projection image corresponding to the selected imaging plane, wherein the projection image comprises a plurality of projection points and each projection point in the projection image is a converted value of the data points of the acquired data.

In another exemplary embodiment, a method for providing a projection image directly from data acquired by a CT scanner is provided. The method comprising: acquiring an amount of data corresponding to an object that is scanned by the CT scanner, wherein the amount of data is generated by an x-ray source that projects a fan beam of x-rays toward a detector array on an opposite side of a gantry of the CT scanner as the object is passed through an opening in the gantry, the acquired amount of data comprising a reconstruction volume; selecting a portion of an imaging region intersecting the reconstruction volume, wherein the selected portion comprises a view of the object inside the reconstruction volume; dividing the imaging region into a plurality of rows and columns, thus creating a grid of points corresponding to the imaging region; determining, for each point in the grid, a data point in the acquired amount of data corresponding to an x-ray source position wherein a ray from the x-ray source to the grid point is closest to a perpendicular orientation with respect to the imaging region, and a detector position where the ray intersects the detector array; and presenting a projection image corresponding to the selected imaging region, wherein the projection image comprises a plurality of projection points and each projection point in the projection image is a converted value of the data points of the acquired data.

Exemplary embodiments of the present invention relate to uses of normalized CT data to images suitable for replacement of scan projection images currently provided by prior baggage inspection systems, wherein the replacement images are calculated directly from selected portions of acquired CT data, instead of reconstructing the volume and projecting an image. Exemplary embodiments produce near-orthographic images that have less distortion than traditional scan projection images.

Other exemplary embodiments of the present invention include a system for acquiring and using the normalized CT data to generate the scan projection images. In yet another exemplary embodiment, a storage medium encoded with machine readable computer program code for providing a scan projection image of an imaging plane of the x-ray projection data is provided.

DETAILED DESCRIPTION OF EXEMPLARY EMBODIMENTS

Figure 1:
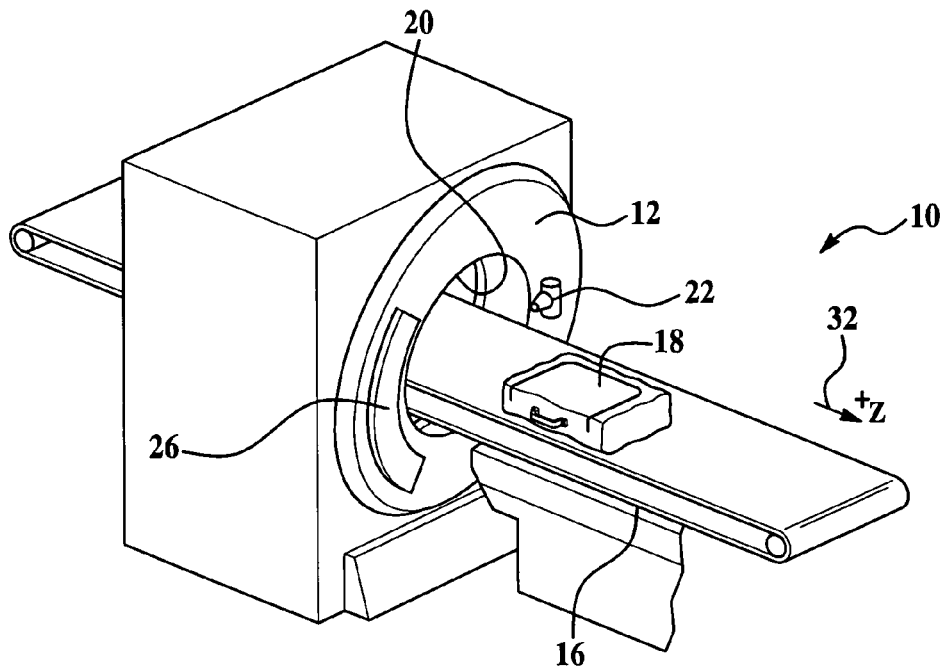
FIGS. 1 and 2 are schematic illustrations of a CT scanning system.

The disclosure of the present invention relates to an apparatus and method for taking normalized data from a spiral CT scanner and creating a high resolution scan projection image directly from the raw data as opposed to reconstructing the entire volume and making a projection through that volume. The following U.S. Pat. Nos. 5,182,764; 5,367,552; 5,960,056; and 6,647,084, the contents each of which are incorporated herein by reference thereto, provide non-limiting examples of Computed Tomography (CT) Systems.

As used herein, raw data refers to the actual data value read from a detector. The raw data depends on the x-ray intensity at the detector, the gain of the detector, and any bias (offset) that is added to the detector value. Furthermore and as also used herein, offset data, gain data, sample data, Xray intensity, normalized data, converted data, x-ray source position, reconstruction circle, and reconstruction volume are as defined as follows:

Offset data: Raw data measurements collected with the x-ray source off.

Gain data: Raw data measurements collected with the xray source on, but with no sample objects in the field of view other than permanently installed objects such as the conveyor belt.

Sample data: Raw data measurements collected with the xray source on and a sample object in the field of view.

Xray intensity: The intensity of the xrays at each detector. X-ray intensity can be computed as K1*(Sample-Offset)/(Gain-Offset). (K1 a calibration constant).

Normalized data: A measure of the attenuation of an xray beam as it travels through an object. Normalized data can be computed as K2*log((Gain-Offset)/(Sample-Offset)), where K2 is a calibration constant and log( ) is the natural logarithm.

Converted data: Any useful representation of the scan data that may be used for a projection image. In the exemplary embodiment of the invention, converted data represents normalized data, but other representations (e.g., Sample data, X-ray intensity) may be used.

X-ray source position: The gantry may make several complete rotations during acquisition, creating a spiral trajectory of the x-ray source when viewed with respect to the moving scanned object. X-ray source position in this discussion refers to a single point in the spiral trajectory.

Reconstruction Circle: A circle defined by the x-ray fan as the x-ray tube rotates around an object. For accurate CT reconstruction, an object must be entirely within the reconstruction circle.

Reconstruction Volume: A cylinder in the scanned object's coordinates defined by the reconstruction circle and the length of the bag for which there is sufficient data to reconstruct.

A major advantage of this process over the prior process is that in the prior process there is a construction of the entire volume of data, which is a very time-consuming event and then there is a projection through this reconstructed image, which is also time consuming. The resulting image of the prior process is of low resolution.

Accordingly, a technical effect or effects of exemplary embodiments of the present invention are directed to providing a projection directly from the normalized data. A detailed description of an embodiment of the present invention is presented herein by way of exemplification and not limitation with reference to FIGS. 1-16.

Figure 2:
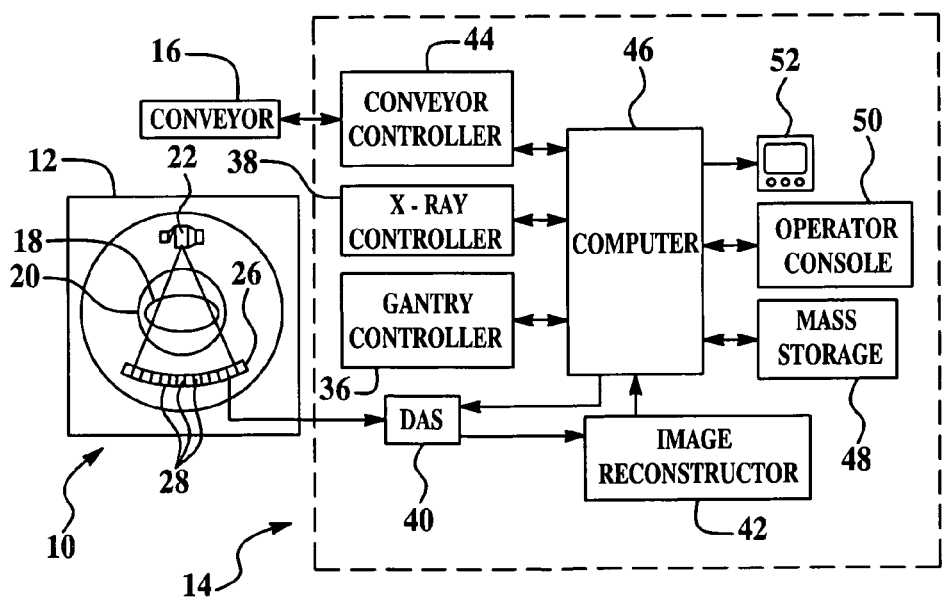

Referring now to FIGS. 1 and 2, a computed tomography (CT) imaging system 10 is shown. CT imaging system 10 is shown having a gantry 12, which is representative of a CT scanner, a control system 14, and a motorized conveyor belt 16 for positioning an object 18, such as a piece of luggage, in gantry opening 20 in gantry 12. Gantry 12 includes an x-ray source 22 that projects a fan beam of x-rays 24 toward a detector array 26 on the opposite side of gantry 12. Detector array 26 is formed by detector elements 28, which are shown in more detail in FIG. 3 and discussed below. Detector elements 28 are radiation detectors that each produces a signal having a magnitude that represents and is dependent on the intensity of the attenuated x-ray beam after it has passed through object 18 being imaged. During a helical scan that acquires x-ray projection data, the gantry along with the x-ray source and detector array rotate within a plane and around the object about a center of rotation 30, while the object is moved through the gantry in a z-direction 32 perpendicular to the plane of rotation. In accordance with an exemplary embodiment, and for most helical scanners the detector array will comprise a plurality of detector rings each having a plurality of detectors, the detector rings having an angular configuration corresponding to the x-ray source.

Gantry 12 and x-ray source 22 are controlled by control system 14, which includes a gantry controller 36, an x-ray controller 38, a data acquisition system (DAS) 40, an image reconstructor 42, a belt controller 44, a computer 46, a mass storage-system 48, an operator interface 50, and a display device 52. The gantry controller controls the rotational speed and position of the gantry, while the x-ray controller provides power and timing signals to the x-ray source, and the data acquisition system acquires analog data from the detector elements and converts the data to digital form for subsequent processing. The image reconstructor receives the digitized x-ray data from the data acquisition system and performs an image reconstruction process that involves filtering the projection data by using a helical reconstruction algorithm.

Computer 46 is in operable communication with the gantry controller, the x-ray controller, and the conveyor controller whereby control signals are sent from the computer to the controllers and information is received from the controllers by the computer. The computer also provides commands and operational parameters to the data acquisition system and receives a reconstructed image data from the image reconstructor. The reconstructed image data is stored by the computer in the mass storage system for subsequent retrieval. An operator interfaces with the computer through the operator interface, which may include, for example, a keyboard and a graphical pointing device, and receives output, such as, for example, a reconstructed image, control settings and other information, on the display device.

Operable communication between the various system elements of FIG. 2 is depicted by arrowhead lines, which illustrate a means for either signal communication or mechanical operation, depending on the system element involved. Operable communication amongst and between the various system elements may be obtained through a hardwired or a wireless arrangement. The computer may be a standalone computer or a network computer and may include instructions in a variety of computer languages for use on a variety of computer platforms, such as, for example, PC, Apple or Sun Microsystems, and under a variety of operating systems, e.g. Windows, MacOS, and Unix or the like. Other examples of the computer include a system having a microprocessor, microcontroller or other equivalent processing device capable of executing commands of computer readable data or program for executing a control algorithm. In order to perform the prescribed functions and desired processing, as well as the computations therefore (e.g., the execution of fourier analysis algorithm(s), the control processes prescribed herein, and the like), the controller may include, but not be limited to, a processor(s), computer(s), memory, storage, register(s), timing, interrupt(s), communication interfaces, and input/output signal interfaces, as well as combinations comprising at least one of the foregoing. For example, the controller may include input signal filtering to enable accurate sampling and conversion or acquisitions of such signals from communications interfaces. As described above, exemplary embodiments of the present invention can be implemented through computer-implemented processes and apparatuses for practicing those processes.

Figure 3:
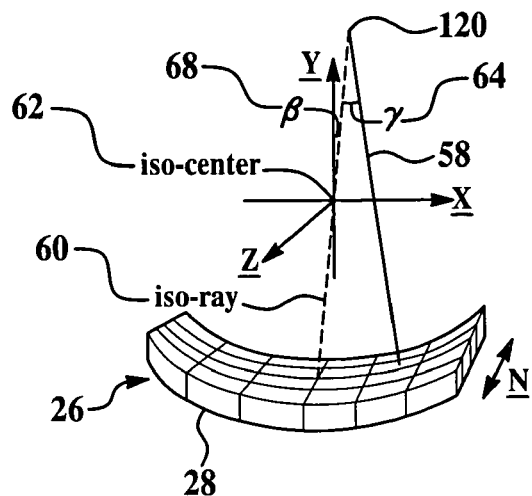
FIG. 3 is a schematic illustration of an x-ray beam and detector array.

Referring now to FIG. 3, an illustration of x-ray beam 58, having a beam axis (iso-ray) 60 that originates at the x-ray source and passes through center of rotation (iso-center) 62, relative to the detector array, having the detector elements arranged in rows n and columns m, is provided. While FIG. 3 depicts only four rows (n=4 for four rings) and six columns (m=6 for six detectors per ring), it will be appreciated that any number of rows and columns may be employed as a matter of design choice. As depicted in FIG. 3, a detector angle γ 64 is shown as an angle formed between detector cell m and the iso-ray which connects the x-ray source and the iso-center, and a projection angle β 68 is shown as an angle formed by the iso-ray with the y-axis.

Figure 4A:
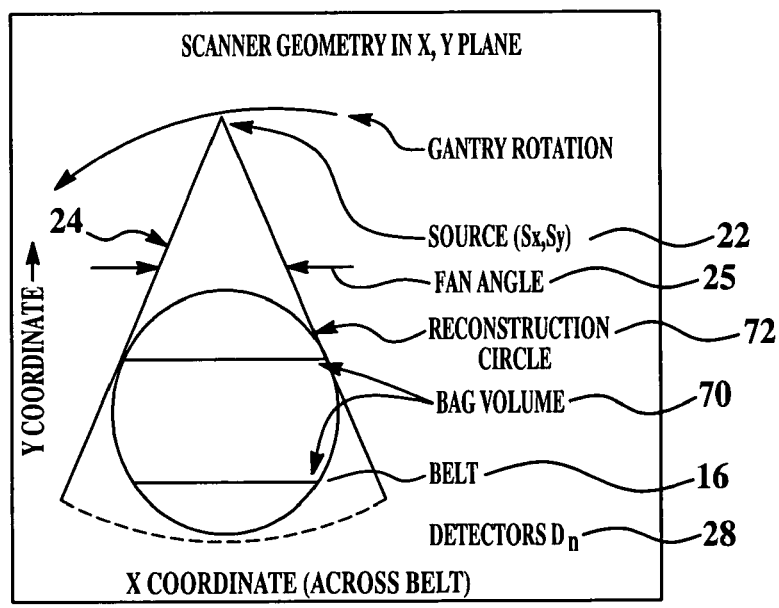
FIGS. 4-12 are various schematic illustrations of fans of x-ray beams acquiring image data in accordance with exemplary embodiments of the present invention.
Figure 4B:
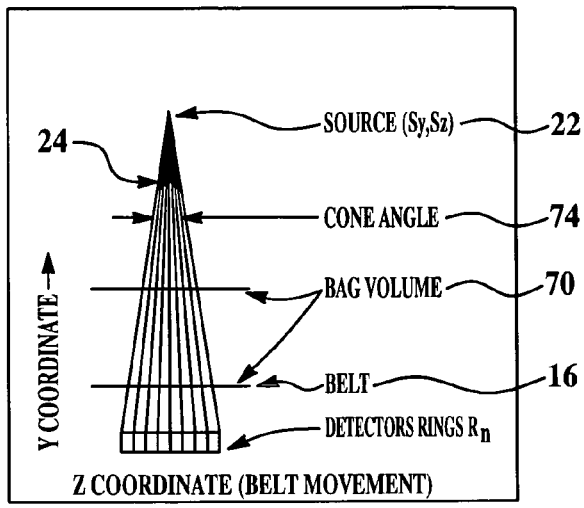

Referring now to FIGS. 4A and 4B, and in accordance with an exemplary embodiment of the present invention, the data acquired at a single x-ray source position is a set of fan beams 24 corresponding to a fan angle 25, with each fan 58 at a slight angle to its neighbor. Also illustrated in FIGS. 4A and 4B is the bag or object volume 70, the conveyor belt, a reconstruction circle 72 and a cone angle 74.

Figure 5:
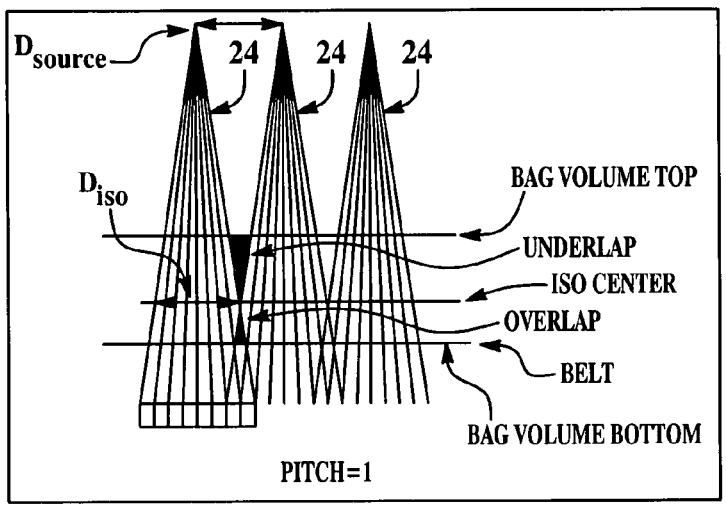

Referring now to FIG. 5, a set of cone beams 24 is illustrated in the reference frame of the moving bag. Each cone represents an x-ray source position in which the x-rays source is straight up, and each successive cone represents one 360 degree rotation of the x-ray source. In FIG. 5, the Pitch of exemplary embodiments of the present invention is illustrated. After one rotation of the x-ray source (e.g., 360 degrees), the bag will have moved some distance $D_{source}$. If $D_{iso}$ is the width of the cone at the isocenter, and $D_{source}$ is the distance that the bag moves in one x-ray source rotation, Pitch is defined as ($D_{source}/D_{iso}$).

Considering the views of FIG. 5 and where the x-ray source is straight up, a pitch of 1 means that at the isocenter there is no overlap or underlap of the cones, but on the belt there is some overlap on each side, and at the top of the bag volume there is some underlap.

Figure 6:
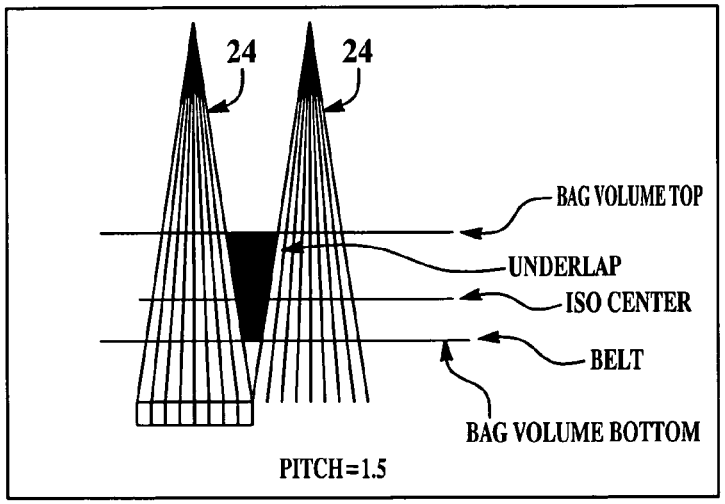
Figure 7:
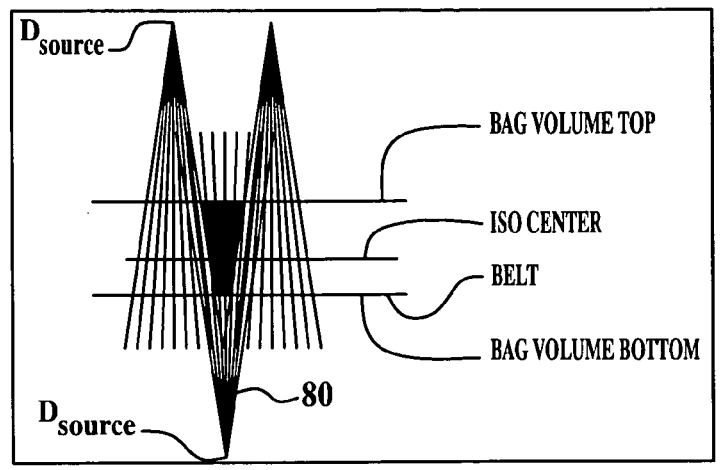

Referring now to FIGS. 6 and 7, it is considered practical to reconstruct at a pitch of 1.5, which results in no overlap or underlap at the detectors, but significant underlap in the bag, especially at the top of the bag. However, the underlap region is covered by the view halfway between, illustrated as view 80, in which the x-ray source has rotated 180 degrees from the first position, and projects rays up instead of down.

Figure 8:
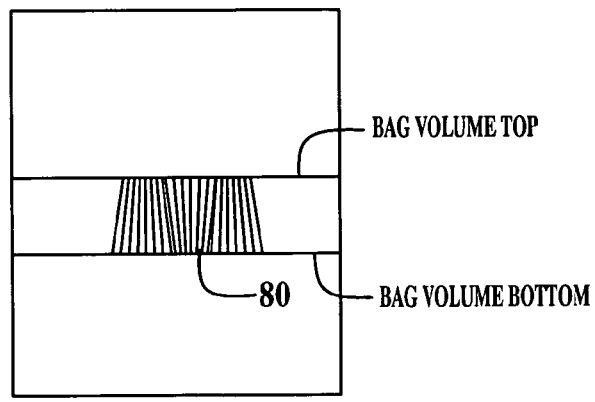

In accordance with an exemplary embodiment a scan projection image is generated from the helical scan data without reconstruction of the entire volume of scanned data and projecting through that volume. Referring now to FIG. 8 and for a region of a vertical plane within the reconstruction circle at X=0 (the set of points that are at the exact center of the belt), a projection of that region onto a line can be constructed by selectively sampling detectors at the center of the detector rings when the x-ray source is either straight up or straight down (e.g., perpendicular or nearly perpendicular to the selected imaging point) and wherein the non-perpendicular detectors are discarded from the data for the selected imaging projection. This sampling method can be thought of as following the side of an accordion. In this projection there is no underlap, the overlapping rays have been discarded, and there are no discontinuities in the projection.

However, parts of the object are sampled more densely than others (the top of the bag when the x-ray source is up, and the bottom of the bag when the x-ray source is down), and there are small amounts of positional distortion. The mean ray angle (in the belt travel direction) is vertical (perpendicular to the belt). Thus, by selecting the perpendicular or near perpendicular rays (e.g., rays on either side of the selected imaging region that are perpendicular or closest to perpendicular) the data selected for conversion with produce a near orthographic image without discontinuities and with minimal distortion.

Figure 9:
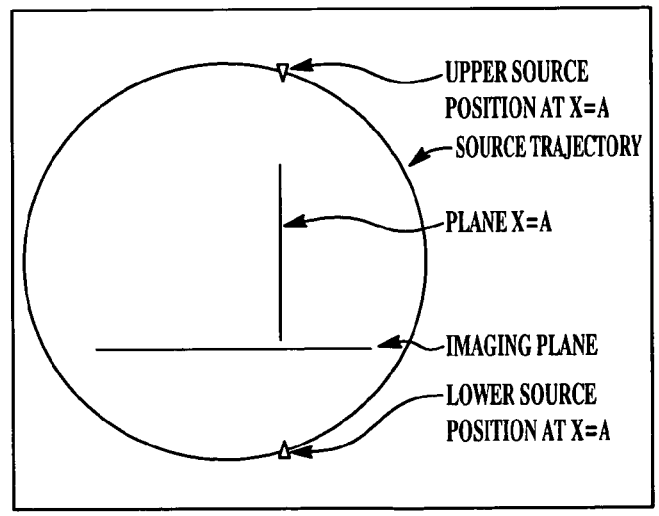
Figure 10:
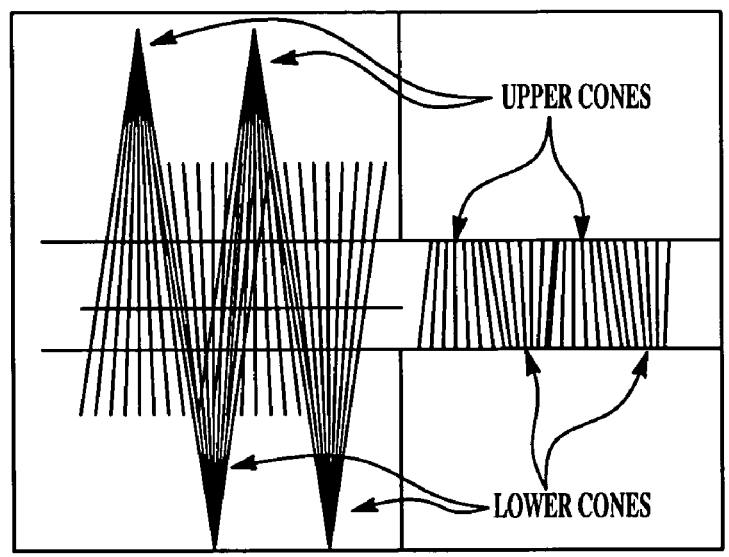
Figure 11:
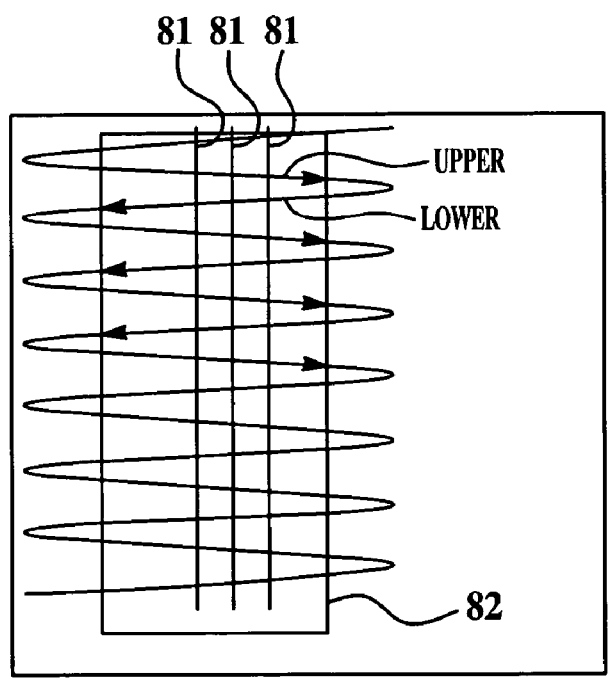

Referring now to FIGS. 9-11, for vertical plane regions not in the center of the belt (X=A) it is still possible to select two x-ray source positions at X=A such that the x-ray source is in the same plane as the region, one above the region and the other below it, and to select detectors along the detector arc which sample rays directly below or directly above the x-ray source, as shown in FIG. 9. Considering the plane X=A, we can again sample points along the upper and lower cone, but the lower cone will no longer be halfway between the two upper cones as the object is moving in the Z direction. This is illustrated schematically in FIG. 10. Here and in accordance with an exemplary embodiment the vertical plane at X=A is also sampled with no underlap, or discontinuity, and there is no overlap because the overlapping rays have been discarded. This provides a set of selected rays. The mean angle of the selected rays is slightly inclined from a line normal to the imaging plane, and the angle of inclination changes across the belt. Thus, and in accordance with an exemplary embodiment of the present invention, near orthographic images of an imaging plane of the object can be produced from the acquired data, wherein the imaging plane may be a view of the object along any angle.

Looking down on the belt, and moving along with the bag as it is being scanned, the x-ray source trajectory is illustrated in FIG. 11. For each vertical line in FIG. 11 (a small representation of which are illustrated as lines 81), the rays are sampled in an accordion fashion, switching between upper and lower x-ray source position. Placing all of the vertical lines together produces a "near orthographic" projection along the indicated region 82 of the horizontal imaging plane.

Figure 12:
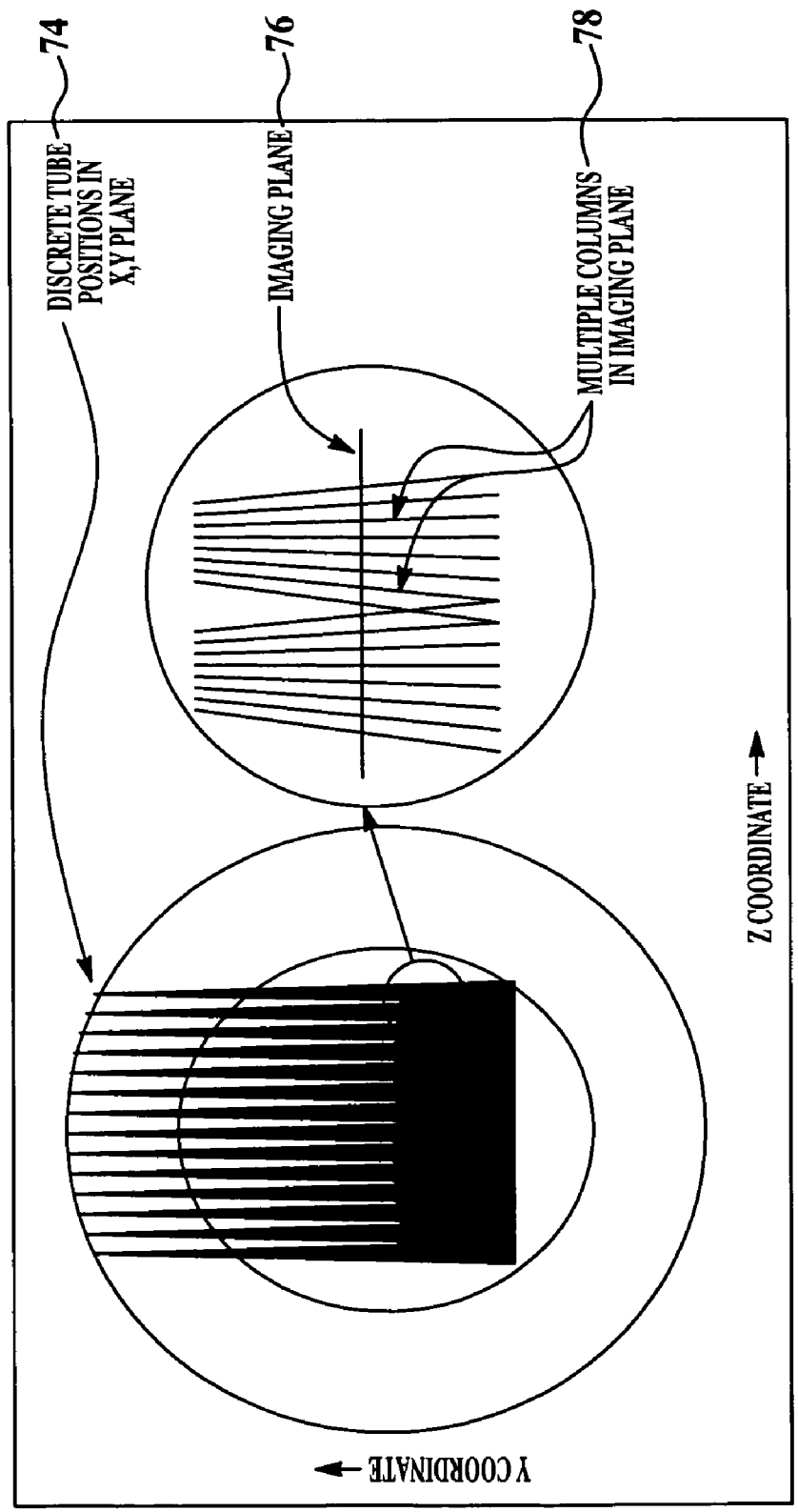

Referring to FIG. 12, the helical data is acquired as a series of views, each of which can be thought of as being acquired from a discrete x-ray source position. Typically the number of views per rotation is a multiple of 360: 720 or 1440, for example. At 1440 views per circle and a 70-degree fan angle, there are only 280 x-ray source positions (74) directly above the reconstruction circle, so an imaging plane region would have only 280 columns of data, resulting in a low resolution image.

However, each detector ring has a large number of detectors—typically 700 to 1000 detectors in the 70-degree arc. Referring to FIG. 12, for each x-ray source position a small number of detectors within the same detector ring define a very narrow fan beam, each ray of which is nearly perpendicular to the imaging plane. The imaging plane region 76 can be divided into a larger number of columns (1000, for example). For each column 78, the ray angle from the source position through the imaging plane at that point is calculated, which determines the appropriate detector to sample. In this manner high resolution across the belt can be achieved. The same process applies for views where the x-ray source is below the imaging plane.

Figure 13:
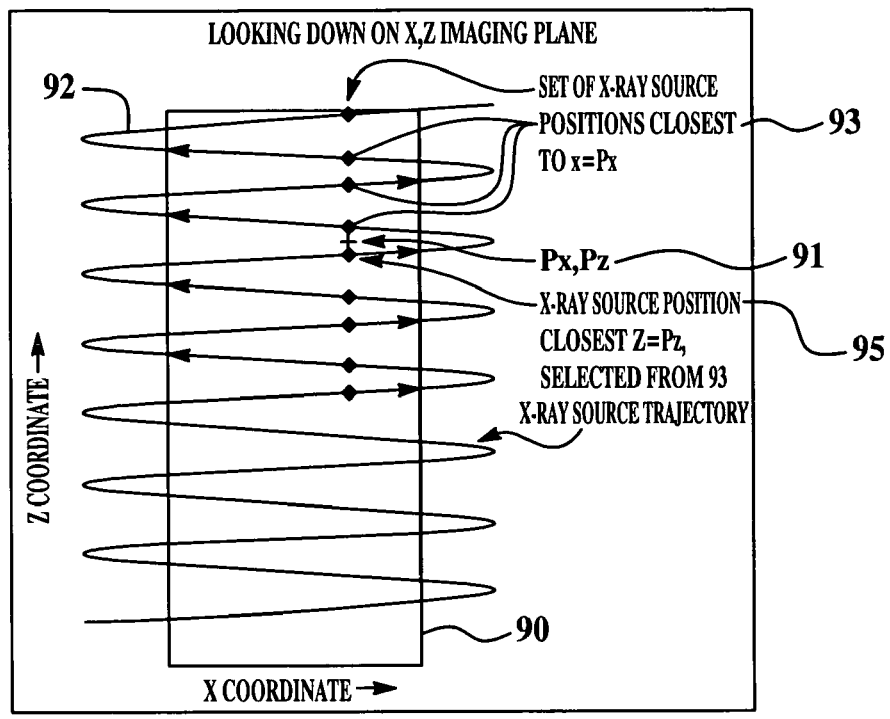
FIGS. 13-16 are various schematic illustrations of operational aspects of exemplary embodiments of the present invention.
Figure 14:
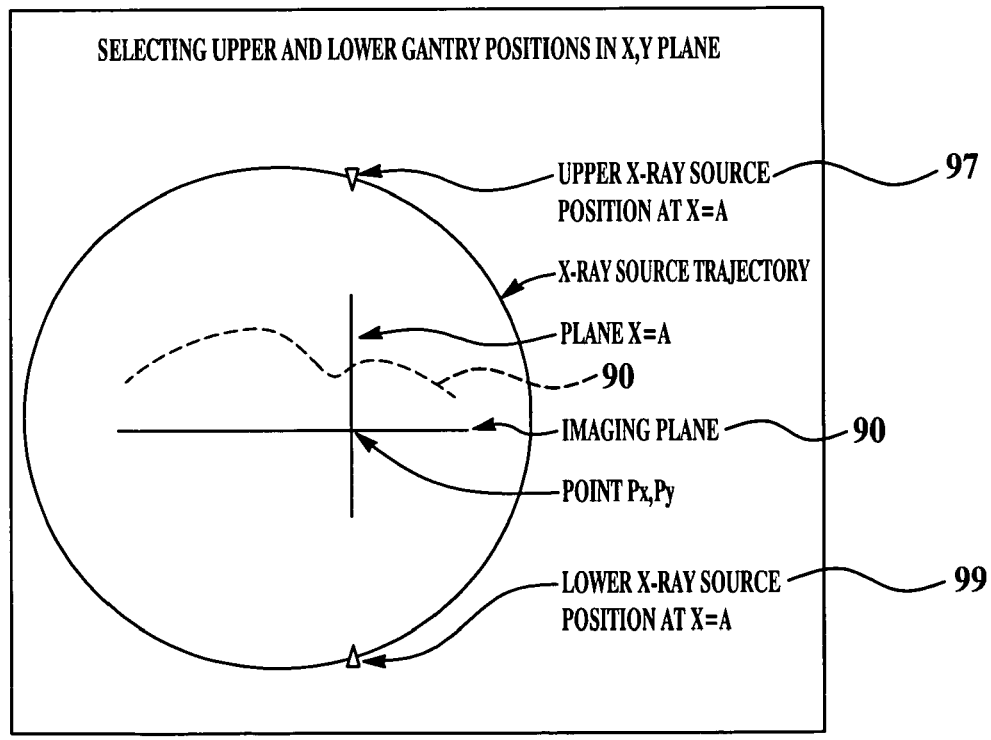
Figure 15:
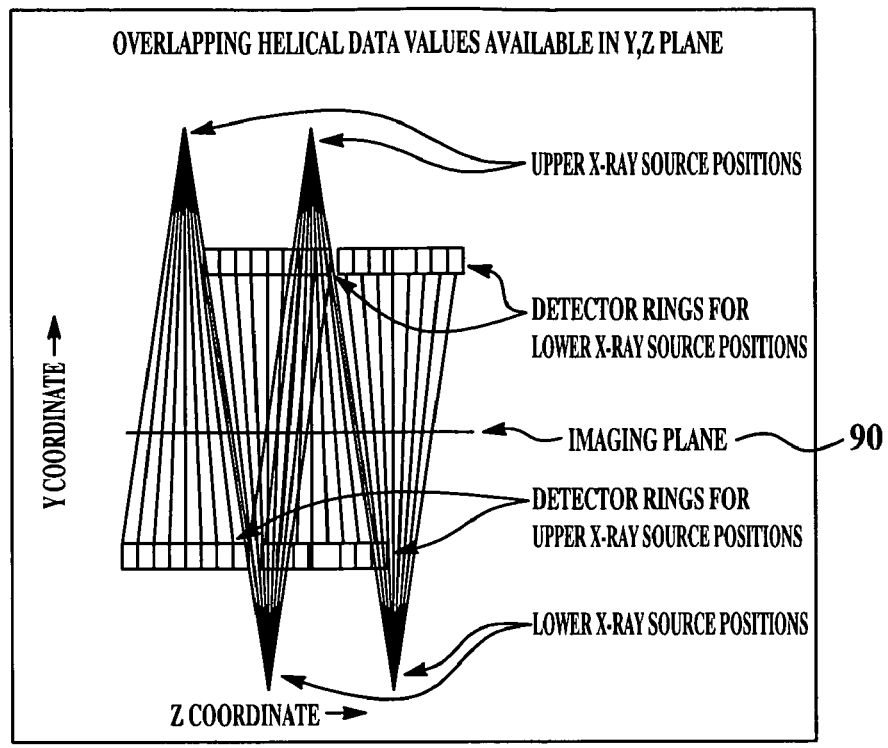
Figure 16:
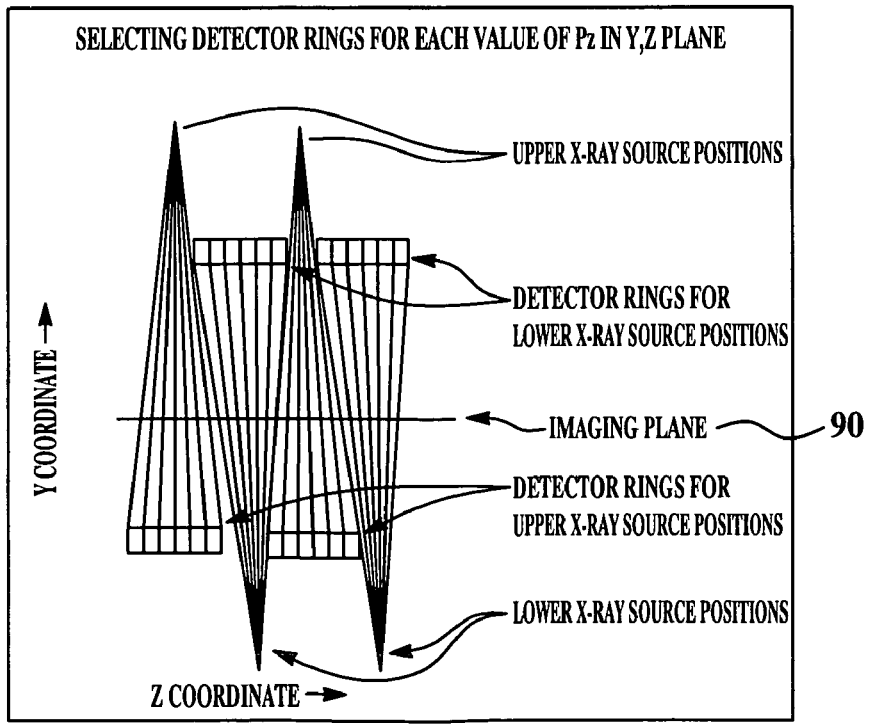

Referring now to FIGS. 13-17, operational aspects of an exemplary embodiment of the present invention is illustrated. In this example and for purpose of clarity a horizontal imaging plane is illustrated but it should be appreciated that any plane region roughly parallel to the Z axis may be selected. In FIG. 13, an X, Z imaging plane 90 is illustrated. Line 92 represents the helical source trajectory of the x-ray device as it rotates within the gantry. Accordingly and as illustrated, numerous passes are made along the X, Z imaging plane. For purposes of description, a point 91 Px, Pz is illustrated on the X, Z imaging plane. For numerous x-ray source positions 93 the x-ray source is at position (Sx,Sy,Sz) such that Sx=Px. Point 95 is selected from points 93 such that Sz is closest to Pz. FIG. 14 shows the X,Y plane of the scanner and illustrates a plane X=A that is normal to the point Px, Pz on the X, Z imaging plane. X-ray source positions 97 (Upper x-ray source position) and 99 (Lower x-ray source position) represent the set of x-ray source positions 93 in which the x-ray source position is at X=A. FIG. 15 illustrates the overlapping helical data values available in the Y, Z plane. As illustrated in FIG. 15, the upper and lower x-ray source positions and detector rings for the upper and lower x-ray source positions are illustrated comprising the overlapping helical data values available in the Y, Z plane. Since there is overlapping helical data only certain detector rings are necessary for Pz in the Y, Z plane. The selected rays (e.g. detector rings) corresponding to the non-overlapping data are illustrated in FIG. 16. Accordingly, for each value of Pz in the Y, Z plane data is available from a plurality of detectors corresponding to upper and lower x-ray source positions. In accordance with an exemplary embodiment the data is available for image projection.

In addition and in an alternative exemplary embodiment, a non-planar surface could be selected as the imaging region. For example, the dashed lines in FIG. 13 illustrate one non-limiting example of a non-planar surface, wherein the aforementioned selection process is utilized to produce a near orthographic image of the imaging region. As in the previous embodiment, the rays are sampled on either side of the non-planar surface wherein near perpendicular rays to the imaging surface are selected and overlapping data from the data rings is discarded based upon the selection of the rays closest to perpendicular to the rows and columns of the imaging region.

Figure 17:
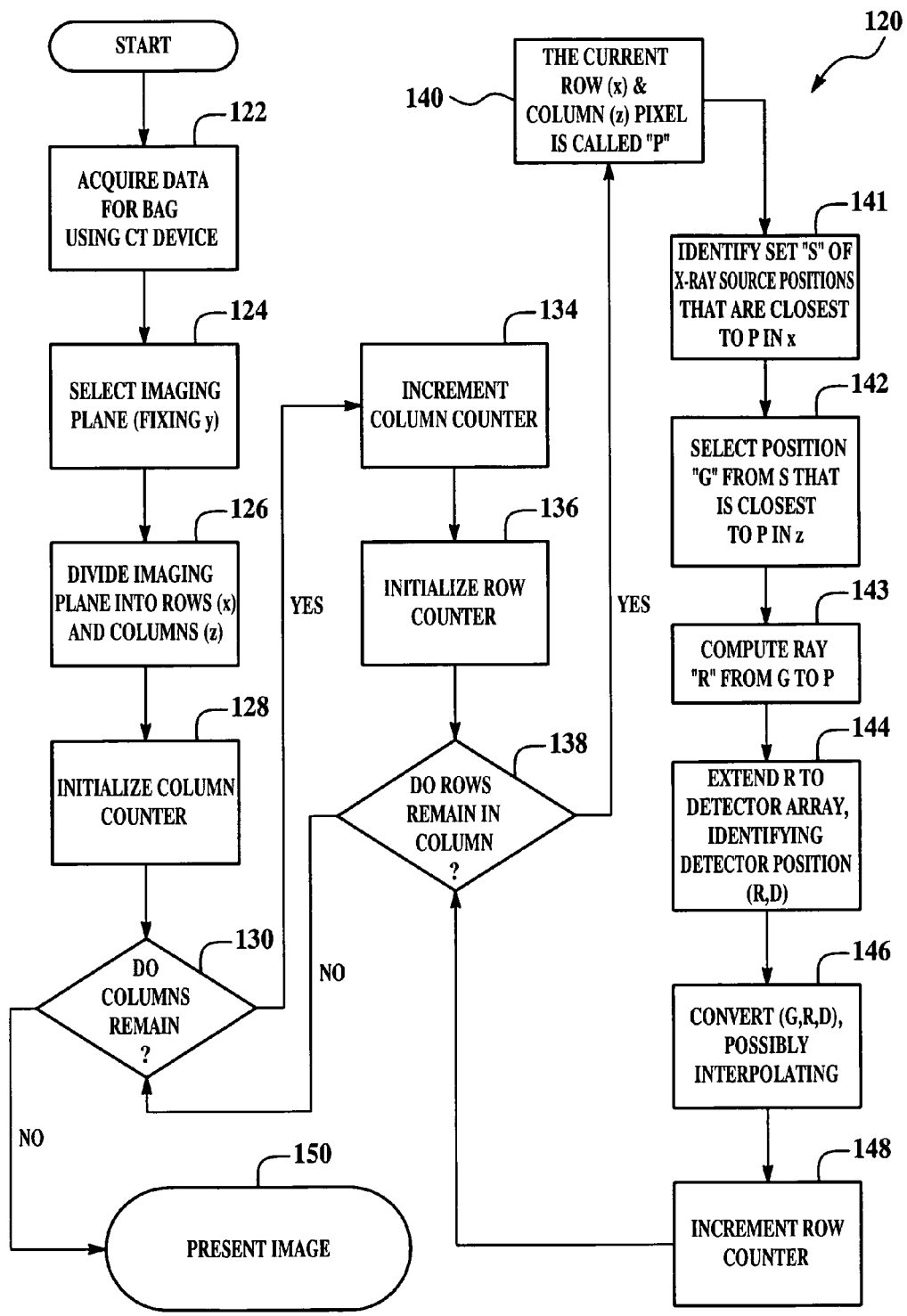
FIG. 17 is a flowchart illustrating portions of a control algorithm for use in exemplary embodiments of the present invention.

Referring now to FIG. 17, a flowchart 120 illustrating portions of a control algorithm for use in exemplary embodiments of the present invention is illustrated. Referring now to step 122 the CT scanner will acquire data for an object being scanned in accordance with third-generation CT scan systems or helical scan systems, as is known to those skilled in the related arts, it being understood that the bag can be moved through the system during a scanning process at a constant or non-constant velocity. In accordance with an exemplary embodiment step 122 represents obtaining some or all of the data for an object being scanned. In other words, it is understood that exemplary embodiments cover algorithms wherein the steps of 124-150 can be performed simultaneously, while the object is still being scanned (e.g., images are capable of being projected prior to completion of the entire scan of the object). A non-limiting example of an object being scanned is a piece of luggage. Assume for this discussion that point Data (Gi,Rj,Dk) represents the data point with the x-ray source at position i, detector ring j, and detector number k.

Referring to step 124, once the data has been acquired for the entire object or alternatively, and as the data is being acquired for the object (e.g., images are capable of being projected prior to completion of the entire scan of the object) an imaging plane is selected (e.g. Y=200 mm or Y=2X+100 mm), either by a predetermined choice or as selected by an operator. For the purpose of clarity in this example, the horizontal imaging plane Y=Py is described; of course the same technique can be applied to any region of a plane that is roughly parallel to the Z axis and is inside the reconstruction circle for the length of the object.

At step 126 the imaging plane is then divided into rows and columns of pixels, which will be used in the control algorithm. For the exemplary horizontal plane, rows have a constant X position, and columns have a constant Z position.

Steps 128 through 138 and step 148 represent the control algorithm process steps for iterating through each column and row of the imaging plane.

Steps 140 through 147 represent the algorithm process steps for each grid point P, where X=Px and Z=Pz. (In this example Y=Py is constant). Step 140 determines P(91, FIG. 13), and the (x,y,z) coordinates of P (Px,Py,Pz).

In step 141, a set of x-ray source positions 93 (FIG. 13) are selected such that the X coordinate of the source is closest to Px. This set of x-ray source positions will alternatively be above and below the imaging plane.

In step 142, a single x-ray source position G (95, FIG. 13) is selected from 93 such that the Z coordinate of the xray source is closest to Pz. At the end of step 142, the line from the source position G to P will be as close to perpendicular to the imaging plane as possible. The source position (G) uniquely determines the subscript i into the CT scan data (Gi,Rj,Dk) as described in step 122.

In step 143, the angle of the ray from the source position (Gx,Gy,Gz) to (Px,Py,Pz) is computed. In step 144 the ray is extended to the point where it hits the detector array, this position on the detector array determines coordinate j for detector row and k for detector number in the CT data (Gi, Rj,Dk). This is illustrated as step 144.

In step 145, the value for the image is computed by selecting and converting the data point (Ai,Rj,Dk) from the CT spiral data. If j or k are not integers, the algorithm may round j and k to the nearest integer and select a single point from the scan data.

Further refinement can be achieved through interpolation. For example, if the above steps compute ring number 2.7 and detector 433.4, the image value at Px,Py can be computed through bilinear interpolation from rings 2 and 3, and detectors 433 and 434. Higher order interpolation may also be used.

In accordance with an exemplary embodiment of the present invention and at each point in the image that is going to be produced the control algorithm selects a ray from the spiral data. In one non-limiting example, and for each row of detectors there is approximately 70 degrees worth of data and there may be anywhere from 700-1000 detectors in a row as well as 64 rows detectors, which provide a large volume of data.

Exemplary embodiments of the present invention create a projection image directly from helical scan data without the need to reconstruct the entire volume. The proposed method is very fast, requiring very little computation. The method uses selective sampling of x-ray detectors at different x-ray source locations such that the selected rays through the object are close to normal to the imaging plane.

The projection image technique of exemplary embodiments of the present invention is limited in resolution in the Z direction (e.g., corresponding to belt movement direction) by the distance between detector rings. The Z resolution is about two-thirds of the distance between detectors rings. If the rings are 3 mm apart then the spatial resolution is close to 2 mm. It is possible to add additional pixels by interpolating between rows. This technique decreases the pixel size, but increases the volume sampled by the interpolated pixel. Similarly, the resolution across the belt is determined by the distance between the detectors within each row of detectors.

The projection image concept of exemplary embodiments of the present invention produces images that will be adequate for operator resolution images. Although there are some distortions in the Z direction, overall there is significantly less distortion than the Scan Projection images that would be produced by a dedicated prescanner; and the images have higher resolution than an image produced by a projection through a reconstructed volume, and are also produced in a much more efficient manner.

Figures 18, 19, 20:
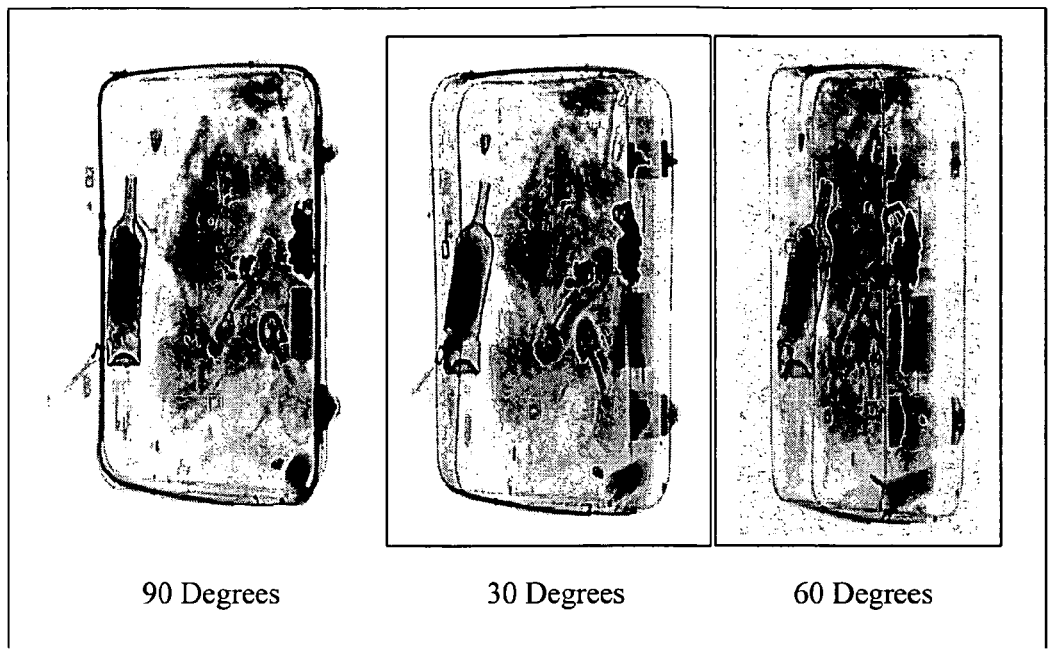
FIGS. 18-20 are views illustrating simulated projection images contemplated in accordance with exemplary embodiment of the present invention.

In addition, the projection image can also be generated quickly for an imaging plane at any angle, which allows 3-Dimensional visualization. Examples of such images are shown in FIGS. 18-20, wherein FIG. 20 clearly shows a bottle 152 is broken, which may be indicative of tampering and possibly a prohibited item.

Accordingly, the projection image can be provided to a sparse slicing inspection algorithm in accordance with an exemplary embodiment of the present invention, in place of a dedicated pre-scan system. A sparse slicing algorithm requires a scan projection (SP) image to select a limited number of slices to reconstruct based on suspect items identified in the SP image, such as bulk objects and vertical sheets. Because it is nearly orthographic, the projection image of exemplary embodiments of the present invention has less distortion than a line scan image, and therefore the mass of suspect items can be more accurately determined.

Although a spiral CT scanner is illustrated, it is understood that exemplary embodiments of the present invention may be used with CT scanners wherein only the x-ray source is rotated about the object being scanned and the detector array is positioned about the gantry opening. In yet another alternative, a plurality of stationary x-ray sources are provided and corresponding detector arrays (e.g., stationary or movable, e.g., rotatable) are positioned to detect the attenuated x-ray beams.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the present application.

What is claimed is:

1. A method for providing a projection image directly from data acquired by a CT scanner, the method comprising:

acquiring data corresponding to an object that is scanned by the CT scanner, wherein the acquired data is generated by an x-ray source that projects a fan beam of x-rays from a plurality of x-ray source positions relative to the object towards a detector array on an opposite side of a gantry of the CT scanner as the object is passed through an opening in the gantry, the acquired data comprising a reconstruction volume;

selecting an imaging plane that intersects the reconstruction volume, at least a portion of the selected imaging plane defined within the reconstruction volume and corresponding to a slice of the object;

dividing the selected imaging plane into a plurality of rows and columns to define a grid of points corresponding to the selected imaging plane, and for each point in the grid of points:

determining an x-ray source position within the plurality of x-ray source positions wherein a ray extending from the x-ray source position to the grid point is closest to a perpendicular orientation with respect to the selected imaging plane;

extending a line from the x-ray source position through the grid point to intersect the detector array at a detector location;

extracting from the data a data point corresponding to the x-ray source position and the detector location; and computing an image pixel value based on the extracted data point; and displaying a projection image based upon image pixel values associated with the grid of points corresponding to the selected imaging plane.

2. The method as in claim 1, wherein the detector array comprises a plurality of detector elements including radiation detectors each configured to produce a signal having a magnitude that represents and is dependent upon an intensity of an attenuated x-ray beam after it has passed through the object as the object is being passed through the gantry and wherein the projection image represents a near orthographic projection through the object onto the imaging plane, and the detector array is a multiple ring detector array.

3. The method as in claim 2, wherein the acquired data does not comprise overlapping attenuated x-ray beams.

4. The method as in claim 3, wherein the projection image is displayed on a display device of the CT scanner and the projection image is displayed before all of the data for the object is acquired by the CT scanner.

5. The method as in claim 1, wherein the step of determining an x-ray source position within the plurality of x-ray source positions further comprises determining the x-ray source position wherein a plurality of fan beams of the x-ray source will be substantially normal to the imaging plane.

6. The method as in claim 5, wherein the CT scanner is a spiral CT scanner and the x-ray source and the detector array are rotated about the object as it is passed through the opening in the gantry.

7. The method as in claim 5, wherein the x-ray source is rotated about the object as it is passed through the opening in the gantry and the detector array comprises a ring of detectors surrounding the opening in the gantry and the ring of detectors remains stationary as the object is scanned by the CT scanner.

8. The method as in claim 5, wherein substantially normal includes fan beams having x-rays orthogonal to the imaging plane as well as x-rays at angles between 75° and 105° with respect to the imaging plane.

9. The method as in claim 1, wherein the acquired data is stored in a storage medium.

10. The method as in claim 1, wherein the acquired data is stored in a central repository, and multiple display devices are provided for multiple projection images along multiple imaging planes of multiple objects.

11. The method as in claim 1, wherein the detector array comprises a plurality of detector elements including radiation detectors each configured to produce a signal having a magnitude that represents and is dependent upon an intensity of an attenuated x-ray beam after it has passed through the object as the object is being passed through the gantry and wherein the acquired data does not comprise overlapping attenuated x-ray beams and the step of selecting an imaging plane further comprises selecting an imaging plane at an arbitrary angle.

12. The method as in claim 1, wherein the x-ray source position may be on either side of the imaging plane.

13. The method as in claim 1, wherein the extracted data point represents a measure of an attenuation of the ray as it travels through the object.

14. The method as in claim 11, wherein the attenuation is determined by K2*log(Gain−Offset)/(Sample−Offset), wherein K2 is a calibration constant, log( ) is the natural logarithm, Offset corresponds to data measurements collected with the x-ray source off, Gain corresponds to data measurements collected with the x-ray source on and no sample objects in a field of view of the x-ray source other than permanently installed objects, and Sample corresponds to data measurements collected with the x-ray source on and a sample object in the field of view of the x-ray source.

15. A storage medium encoded with machine readable computer program code for providing a scan projection image of an imaging plane of an object that is scanned by a CT scanner, the storage medium including instructions for causing a computer to implement a method comprising:

acquiring data corresponding to the object, wherein the acquired data is generated by an x-ray source that projects a fan beam of x-rays from a plurality of x-ray source positions relative to the object toward a detector array on an opposite side of a gantry of the CT scanner as the object is passed through an opening in the gantry, the acquired data comprising a reconstruction volume;

selecting an imaging plane that intersects the reconstruction volume, at least a portion of the selected imaging plane defined within the reconstruction volume, the selected imaging plane corresponding to a slice of the object;

dividing the selected imaging plane into a plurality of rows and columns to define a grid of points corresponding to the selected imaging plane, and for each point in the grid of points;

determining an x-ray source position within the plurality of x-ray source positions wherein a ray extending from the x-ray source position to the grid point is closest to a perpendicular orientation with respect to the selected imaging plane;

extending a line from the x-ray source position through the grid point to intersect the detector array at a detector location;

extracting from the acquired data a data point corresponding to the x-ray source position and the detector location; and computing an image pixel value based on the extracted data point; and displaying a projection image based upon image pixel values associated with the grid of points corresponding to the selected imaging plane.

16. The storage medium as in claim 15, wherein the detector array comprises a plurality of detector elements including radiation detectors each configured to produce a signal having a magnitude that represents and is dependent upon an intensity of an attenuated x-ray beam after it has passed through the object as the object is being passed through the gantry and wherein the x-ray source position is one of above and below the imaging plane, the projection image representing a near orthographic projection through the object onto the imaging plane.

17. The storage medium as in claim 16, wherein the acquired data does not comprise overlapping attenuated x-ray beams.

18. The storage medium as in claim 16, wherein the step of determining an x-ray source position within the plurality of x-ray source positions further comprises determining the x-ray source position wherein a plurality of fan beams of the x-ray source will be substantially normal to the imaging plane, wherein substantially normal includes fan beams having x-rays orthogonal to the imaging plane as well as x-rays at angles between 75° and 105° with respect to the imaging plane.

19. The storage medium as in claim 16, wherein the detector array comprises a plurality of detector elements including radiation detectors each configured to produce a signal having a magnitude that represents and is dependent upon an intensity of an attenuated x-ray beam after it has passed through the object as the object is being passed through the gantry and wherein the acquired data does not comprise overlapping attenuated x-ray beams and the step of selecting the imaging plane further comprises selecting an imaging plane at an arbitrary angle and the projection image is displayed before all of the data for the object is acquired by the CT scanner.

20. The storage medium as in claim 15, wherein the CT scanner is a spiral CT scanner and the x-ray source and the detector array are rotated about the object as it is passed through the opening in the gantry.

21. The storage medium as in claim 15, wherein the x-ray source is rotated about the object as it is passed through the opening in the gantry and the detector array comprises a ring of detectors surrounding the opening in the gantry and the ring of detectors remains stationary as the object is scanned by the CT scanner.

22. A computed tomography system for providing a scan projection image directly from data acquired by the system, the system comprising:
   a CT scanner, configured to produce x-ray projection data as an object is passed through the CT scanner;
   a storage medium encoded with machine readable computer program code, the storage medium including instructions for causing a computer to implement a method comprising:
   acquiring data corresponding to the object, wherein the acquired data is generated by an x-ray source that projects a fan beam of x-rays from a plurality of x-ray source positions relative to the object toward a detector array on an opposite side of a gantry of the CT scanner as the object is passed through an opening in the gantry, the acquired data comprising a reconstruction volume;
   selecting an imaging plane that intersects the reconstruction volume, at least a portion of the selected imaging plane defined within the reconstruction volume, the selected imaging plane corresponding to a slice of the object;
   dividing the selected imaging plane into a plurality of rows and columns, thus creating a grid of points corresponding to the selected imaging plane, and for each point in the grid of points:
      determining an x-ray source position within the plurality of x-ray source positions wherein a ray extending from the x-ray source position to the grid point is closest to a perpendicular orientation with respect to the selected imaging plane;
      extending a line from the x-ray source position through the grid point to intersect the detector array at a detector location;
      extracting from the acquired data a data point corresponding to the x-ray source position and the detector location; and
      computing an image pixel value based on the extracted data point; and
   displaying a projection image based upon image pixel values associated with the grid of points corresponding to the selected imaging plane.

23. The system as in claim 22, wherein the detector array comprises a plurality of detector elements that are radiation detectors each being configured to produce a signal having a magnitude that represents and is dependent upon an intensity of an attenuated x-ray beam after it has passed through the object as it is being passed through the gantry, and the detector array is a multiple ring detector array.

24. The system as in claim 22, wherein the acquired data does not comprise overlapping attenuated x-ray beams and wherein the x-ray source position is one of above and below the imaging plane.

25. The system as in claim 22, wherein the step of determining an x-ray source position within the plurality of x-ray source positions further comprises determining the x-ray source position wherein a plurality of fan beams of the x-ray source will be substantially normal to the imaging plane, wherein substantially normal includes fan beams having x-rays orthogonal to the imaging plane as well as x-rays at angles between 75° and 105° with respect to the imaging plane.

26. The system as in claim 22, wherein the detector array comprises a plurality of detector elements including radiation detectors each configured to produce a signal having a magnitude that represents and is dependent upon an intensity of an attenuated x-ray beam after it has passed through the object as the object is being passed through the gantry and wherein the acquired data does not comprise overlapping attenuated x-ray beams and the step of selecting the imaging plane further comprises selecting an imaging plane at an arbitrary angle and the projection image is displayed before all of the data for the object is acquired by the CT scanner.

27. The system as in claim 22, wherein the acquired data is stored in a central repository, and multiple display devices are provided for multiple projection images along multiple imaging planes of multiple objects.

28. The system as in claim 22, wherein the CT scanner is a spiral CT scanner and the x-ray source and the detector array are rotated about the object as it is passed through the opening in the gantry.

29. The system as in claim 22, wherein the x-ray source is rotated about the object as it is passed through the opening in the gantry and the detector array comprises a ring of detectors surrounding the opening in the gantry and the ring of detectors remains stationary as the object is scanned by the CT scanner.

30. A method for providing a projection image directly from data acquired by a CT scanner, the method comprising:
   acquiring data corresponding to an object that is scanned by the CT scanner, wherein the data is generated by an x-ray source that projects a fan beam of x-rays from a plurality of x-ray source positions relative to the object toward a detector array on an opposite side of a gantry of the CT scanner as the object is passed through an opening in the gantry, the acquired data comprising a reconstruction volume;
   selecting an imaging region that intersects the reconstruction volume, the selected imaging region including a region of the object within the reconstruction volume;
   dividing the selected imaging region into a plurality of rows and columns to define a grid of points corresponding to the selected imaging region, and for each point in the grid of points:
      determining an x-ray source position within the plurality of x-ray source positions wherein a ray extending from the x-ray source position to the grid point is closest to a perpendicular orientation with respect to the selected imaging region;
      extending a line from the x-ray source position through the grid point to intersect the detector array at a detector location;
      extracting from the acquired data a data point corresponding to the x-ray source position and the detector location; and
      computing an image pixel value based on the extracted data point; and
   displaying a projection image based upon image pixel values associated with the grid of points corresponding to the selected imaging region.

31. The method as in claim 30, wherein the imaging region is non planar.

* * * * *